(12) United States Patent
Qi et al.

(10) Patent No.: US 12,264,118 B2
(45) Date of Patent: Apr. 1, 2025

(54) PROCESS FOR PRODUCING LOWER OLEFINS FROM OXYGENATES

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Guozhen Qi, Shanghai (CN); Jing Cao, Shanghai (CN); Xiaohong Li, Shanghai (CN); Hongtao Wang, Shanghai (CN); Yongming Jin, Shanghai (CN); Pan Gao, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(*) Notice: Subject to any disclaimer, the term of this patent is extended or adjusted under 35 U.S.C. 154(b) by 320 days.

(21) Appl. No.: 17/906,230

(22) PCT Filed: Mar. 11, 2021

(86) PCT No.: PCT/CN2021/080114
§ 371 (c)(1),
(2) Date: Sep. 13, 2022

(87) PCT Pub. No.: WO2021/180150
PCT Pub. Date: Sep. 16, 2021

(65) Prior Publication Data
US 2023/0118436 A1  Apr. 20, 2023

(30) Foreign Application Priority Data

Mar. 13, 2020 (CN) .................. 202010173926.6
Mar. 13, 2020 (CN) .................. 202010173939.3

(51) Int. Cl.
*C07C 1/22* (2006.01)
*B01D 45/16* (2006.01)
(Continued)

(52) U.S. Cl.
CPC ............. *C07C 1/22* (2013.01); *B01D 45/16* (2013.01); *B01J 8/1827* (2013.01); *B01J 8/24* (2013.01); *C07C 2529/89* (2013.01)

(58) Field of Classification Search
CPC ............. C07C 1/22; C07C 2529/89; C07C 2529/85; C07C 1/20; B01D 45/16; B01J 8/1827;
(Continued)

(56) References Cited

U.S. PATENT DOCUMENTS

| 4,499,327 A | 2/1985 | Kaiser |
| 6,166,282 A | 12/2000 | Miller |

FOREIGN PATENT DOCUMENTS

| CN | 101260013 A | 9/2008 |
| CN | 101293803 A | 10/2008 |

(Continued)

OTHER PUBLICATIONS

Translation of CN 101318870 A (Year: 2008).*
(Continued)

*Primary Examiner* — Ali Z Fadhel
(74) *Attorney, Agent, or Firm* — Panitch Schwarze Belisario & Nadel LLP (57) ABSTRACT

A process for producing lower olefins from oxygenates includes the steps of contacting a feedstock comprising oxygenates with molecular sieve catalyst in fluidized bed
(Continued)

reaction zone under effective conditions, to produce product including ethylene and/or propylene; the effective conditions include that in the fluidized bed reaction zone, the weights of catalysts having various carbon deposition amounts are controlled, calculated as the weight of the molecular sieve in the catalysts, to have the following proportions based on the total weight of the catalysts in the fluidized bed reaction zone: the proportion of the weight of the catalyst having a coke deposition amount of less than 3 wt % is 1-20 wt %; the catalyst having a coke deposition amount of from 3 wt % to less than 5 wt % represents 10 to 70 wt %; and the catalyst having a coke deposition amount from 5 wt % to 10 wt % represents 10 to 88 wt %.

18 Claims, 1 Drawing Sheet

(51) Int. Cl.
  *B01J 8/18* (2006.01)
  *B01J 8/24* (2006.01)
(58) Field of Classification Search
  CPC .............. B01J 8/24; B01J 2208/009891; B01J 8/0055; B01J 8/125; B01J 8/1863; B01J 8/30; B01J 29/85; B01J 29/90; Y02P 20/52; Y02P 20/584; Y02P 30/20; Y02P 30/40

See application file for complete search history.

(56) References Cited

FOREIGN PATENT DOCUMENTS

| | | |
|---|---|---|
| CN | 101318870 A | 12/2008 |
| CN | 101328103 A | 12/2008 |

OTHER PUBLICATIONS

International Search Report (PCT/ISA/210) with an English translation, and Written Opinion (PCT/ISA/237) mailed on Jun. 9, 2021, by the China National Intellectual Property Administration as the International Searching Authority for International Application No. PCT/CN2021/080114.

* cited by examiner

PROCESS FOR PRODUCING LOWER OLEFINS FROM OXYGENATES

TECHNICAL FIELD

The invention relates to a process for producing lower olefins by using oxygenates.

BACKGROUND

Lower olefins comprise mainly ethylene and propylene, which are two important basic chemical raw materials, and the demand of the lower olefins is increasing continuously. Generally, ethylene and propylene are produced through petroleum routes, but the cost of producing ethylene and propylene from petroleum resources is increasing due to the limited supply and high price of petroleum resources. In recent years, technologies for producing ethylene and propylene by conversion of raw materials replacing of petroleum have been actively developed. Among others, an important alternative raw material for producing lower olefins is oxygenates, such as alcohols (methanol and ethanol), ethers (dimethyl ether and methyl ethyl ether), esters (dimethyl carbonate and methyl formate), and the like, which can be converted from energy sources such as coal, natural gas and biomass. Certain oxygenates have been produced on a larger scale, such as methanol, from coal or natural gas, in a well-established process that can be scaled up to millions of tons. Due to the wide range of oxygenate sources, in combination with the economics of the processes for conversion to lower olefins, the processes for the conversion of Oxygenates To Olefins (OTO), particularly the conversion of Methanol To Olefins (MTO), are receiving increasing attention.

Document U.S. Pat. No. 4,499,327 makes detailed studies on the application of a silicoaluminophosphate molecular sieve catalyst in a process for preparing olefins by methanol conversion, and proposes SAPO-34 as a preferred catalyst for an MTO process. The SAPO-34 catalyst has high selectivity and activity for lower olefin, and can ensure that the reaction duration for converting methanol to the lower olefin is less than 10 seconds, even up to reach the reaction duration range of a riser.

Document U.S. Pat. No. 6,166,282 discloses a technology and reactor for converting methanol to lower olefins, which uses a fast fluidized bed reactor, wherein after the gas phase is reacted in a dense phase reaction zone having a lower gas velocity, the gas phase rises to a fast separation zone having a dramatically reduced inner diameter, and a special gas-solid separation device is used for primarily separating most of the entrained catalysts. As the product gas and the catalyst are rapidly separated after the reaction, the occurrence of secondary reaction is effectively prevented. Through simulation calculation, it can be seen that compared with the traditional bubbling fluidized bed reactor, the internal diameter of the fast fluidized bed reactor and the required inventory of the catalyst are greatly reduced. The carbon-based yield of the lower olefin in the process is generally about 77%.

Document CN101328103A discloses a process for converting methanol or dimethyl ether to lower olefins, which comprises feeding a raw material of methanol or dimethyl ether into a reaction zone of a fluidized bed reactor, and contacting the raw material with a catalyst comprising a silicoaluminophosphate molecular sieve; wherein the average density of the reaction zone is 20-300 kg/m$^3$, and the average coke deposition amount of the catalyst in the reaction zone is 1.5-4.5% by weight, under the conditions of a gauge pressure of 0.05-1 MPa, an average temperature of the reaction zone of 450-550° C., and an average superficial gas velocity of the reaction zone of 0.8-2.0 m/s. The carbon-based selectivity of the lower olefin reaches up to 81.51 wt %.

However, with the increasing demand of ethylene and propylene in the market, higher requirements are raised on the production technology of the lower olefins.

SUMMARY OF THE INVENTION

The inventors of the invention discover that in the process of converting oxygenates (especially methanol) to lower olefins in the prior art, a certain amount of coke deposition is necessary for ensuring high selectivity to lower olefins. In a fluidized bed reactor, a catalyst circulation between reaction and regeneration exists, such that the problem involving mixing of multiple strands of catalysts is inevitably existing in the reaction zone, while the coke deposition amount of the catalysts in the reaction zone is actually an average value, wherein the quality of mixing of the low-carbon-deposition-amount catalysts and the high-carbon-deposition-amount catalysts is crucial for improving the selectivity to the lower olefins.

Based on the discovery, the inventors of the present invention further discover that the reaction performances of the raw material on catalysts with different amounts of coke deposition are greatly different. Especially, when the catalyst has a coke deposition amount of less than 3 wt %, the selectivity to the lower olefins is greatly reduced, whilst it is necessary for the catalyst to have a coke deposition amount less than 3 wt % to ensure a high conversion of the feedstock. An effective method for solving the contradiction is to control the content of the low-carbon-deposition-amount catalyst and the distribution thereof in the reaction zone, and to match and control the concentration of the catalyst in the reaction zone, which can ensure both high conversion of methanol and high selectivity to lower olefins. Furthermore, the inventors have surprisingly found that controlling the difference in the coke deposition amounts of the mixed catalysts in the reaction zone effectively is crucial for achieving the desired technical effect.

The present invention has been completed based on these discoveries.

Specifically, the present invention provides, for example, embodiments of:

1. A process for producing lower olefins from oxygenates, comprising the steps of contacting a feedstock comprising oxygenates with a molecular sieve catalyst in a fluidized bed reaction zone under effective conditions, to produce a product comprising ethylene and/or propylene;

the effective conditions comprise that in the fluidized bed reaction zone, the weights of catalysts having various coke deposition amounts are controlled, calculated as the weight of the molecular sieve in the catalyst, to have the following proportions based on the total weight of the catalysts in the fluidized bed reaction zone:

the proportion of the weight of the catalyst having a coke deposition amount of less than 3 wt % is 1-20 wt %, preferably 1-15 wt %, 1.5-10 wt %, or 2-5 wt %, based on the total weight of the catalysts in the fluidized bed reaction zone;

the catalyst having a coke deposition amount of from 3 wt % to less than 5 wt % represents 10 to 70 wt %, preferably 15 to 60 wt %, 20 to 50 wt %, or 30 to 45 wt %, based on the total weight of the catalysts;

the catalyst having a coke deposition amount from 5 wt % to 10 wt % represents 10 to 88 wt %, preferably 15 to 80 wt %, 20 to 70 wt %, or 30 to 60 wt %, based on the total weight of the catalysts.

2. The process of embodiment 1, wherein the ratio of the volume of the gas phase in the fluidized bed reaction zone to the volume of the total catalyst in the fluidized bed reaction zone is from 1 to 15, preferably from 5 to 12.

3. The process of embodiment 1 or 2, wherein the feedstock is fed through a distributor into the reaction zone of the fluidized bed reactor, wherein the coke deposition amounts on the catalyst particles within the height range from the distributor up to a height at ½ bed height vary to have a maximum difference of less than 8 wt %, preferably less than 5 wt %, or less than 3 wt %.

4. The process of embodiment 3, wherein the coke deposition amounts on the catalyst particles within the height range from the distributor up to a height at ½ bed height vary to have a maximum difference of greater than 0.1 wt %.

5. A process for producing lower olefins from oxygenates, comprising the steps of: contacting the oxygenate feedstock with a molecular sieve catalyst in a fluidized bed reaction zone under effective conditions, to produce an ethylene and/or propylene containing product;
wherein the feedstock is fed into the fluidized bed reactor reaction zone through a distributor, wherein the coke deposition amounts on the catalyst particles within the height range from the distributor up to a height at ½ bed height vary to have a maximum difference of less than 8 wt %, preferably less than 5 wt %, or less than 3 wt %.

6. The process of embodiment 5, wherein the coke deposition amounts on the catalyst particles within the height range from the distributor up to a height at ½ bed height vary to have a maximum difference of greater than 0.1 wt %.

7. The process of embodiment 5 or 6, wherein the effective conditions comprise that in the fluidized bed reaction zone, the weights of catalysts having various coke deposition amounts are controlled, calculated as the weight of the molecular sieve in the catalysts, to have the following proportions based on the total weight of the catalysts in the fluidized bed reaction zone:

the proportion of the weight of the catalyst having a coke deposition amount of less than 3 wt % is 1-20 wt %, preferably 1-15 wt %, 1.5-10 wt %, or 2-5 wt %, based on the total weight of the catalysts in the fluidized bed reaction zone;

the catalyst having a coke deposition amount of from 3 wt % to less than 5 wt % represents 10 to 70 wt %, preferably 15 to 60 wt %, 20 to 50 wt %, or 30 to 45 wt %, based on the total weight of the catalysts;

the catalyst having a coke deposition amount from 5 wt % to 10 wt % represents 10 to 88 wt %, preferably 15 to 80 wt %, 20 to 70 wt %, or 30 to 60 wt %, based on the total weight of the catalysts.

8. The process of embodiment 7, wherein the ratio of the volume of the gas phase in the fluidized bed reaction zone to the volume of the total catalyst in the fluidized bed reaction zone is from 1 to 15, preferably from 5 to 12.

9. The process of any one of the preceding embodiments, wherein the oxygenate feedstock comprises methanol.

10. The process of any one of the preceding embodiments, wherein the molecular sieve is a silicoaluminophosphate molecular sieve, preferably SAPO-18, SAPO-34, SAPO-5, or a combination thereof.

11. The process of any one of the preceding embodiments, wherein the fluidized bed reaction zone is in the form of a dense phase fluidized bed, turbulent fluidized bed, or fast fluidized bed, preferably a fast fluidized bed.

12. The process of any one of the preceding embodiments, wherein the effective conditions further comprise: a reaction temperature of 400-550° C., and a reaction pressure of 0-1 MPaG.

13. The process of any one of the preceding embodiments, wherein the difference of the coke deposition amounts between the spent catalyst and the regenerated catalyst is not more than 7 wt %, preferably not more than 6 wt %, more preferably not more than 5 wt %.

14. The process of any one of the preceding embodiments, wherein the catalyst having a coke deposition amount of less than 3 wt % is uniformly distributed within the fluidized bed reaction zone.

15. The process of any one of the preceding embodiments, wherein the gas phase and the catalyst within the fluidized bed reaction zone are rapidly separated by a separation device subsequent to the reaction or after leaving the fluidized bed reaction zone.

Preferably, according to an exemplary embodiment of the present invention, the lower portion of the reaction zone is equipped with a regeneration inclined line outlet, the regeneration inclined line outlet is equipped with a catalyst distributor, and the catalyst distributor is substantially horizontally arranged along the radial direction of the reaction zone.

16. The process of any one of embodiments 3-15, wherein the spent catalyst is derived from deactivation of the catalyst in the reaction zone, the spent catalyst is introduced into a regenerator through a inclined line to be regenerated to form a regenerated catalyst, and the regenerated catalyst is returned to the fluidized bed reaction zone through a regeneration inclined line; wherein the ratio of the regenerated catalyst to the spent catalyst in the reaction zone is controlled to be 0.01-1, preferably 0.05-0.5, and more preferably 0.07-0.3; and the coke deposition amount on the regenerated catalyst is 0 to 5 wt %, preferably 0.05 to 3 wt %, more preferably 0.5 to 2 wt %.

17. A fluidized bed reactor for carrying out the process of any one of the preceding embodiments for producing lower olefins from oxygenates, comprising:

a reaction zone, for receiving methanol feedstock and contacting it with catalyst to produce olefins product, wherein the process deactivates, at least in part, the catalyst to produce spent catalyst;

a gas-solid rapid separation device, for separating the spent catalyst from the reaction zone;

a cyclone separator, for receiving the gas-phase product separated by the gas-solid rapid separation device and a part of the spent catalyst not separated by the gas-solid rapid separation device, so as to carry out a secondary separation;

a stripping zone, for receiving the spent catalyst from the dipleg of the cyclone; and an external circulation inclined line for catalyst, for returning at least a part of stripped spent catalyst from the stripping zone to the bottom of the reaction zone.

DESCRIPTION OF DRAWINGS

In FIG. 1:
1 denotes a feeding line for feedstocks of the reactor;
2 denotes a reaction zone of the reactor;
3 denotes a gas-solid rapid separation zone;
4 denotes a stripping zone;
5 denotes an external circulation inclined line of the reactor;
6 denotes a feedstock distributor;
8 denotes a gas-solid cyclone separator of the reactor;
9 denotes a separation zone of the reactor;
11 denotes a product gas outlet line;
14 denotes a spent inclined line;
15 denotes a regeneration inclined line;

TECHNICAL EFFECTS

According to the process of the present invention, not only high conversion of raw materials can be ensured, but also high selectivity to the lower olefins can be ensured, where the selectivity to the lower olefins can reach 84% or more.

EMBODIMENTS OF THE INVENTION

The present invention will be further illustrated in more detail below, while it should be understood that the scope of the invention is not restricted by the embodiments, but is defined by the appended claims.

All publications, patent applications, patents, and other references mentioned in this specification are herein incorporated by reference in their entirety. Unless defined specifically, all technical and scientific terms used herein have the same meaning as commonly understood by those skilled in the art to which this invention belongs. In case of conflict, the present specification, including definitions, will control.

When the present specification mentions a material, substance, method, step, device, or component, etc. with the derivative words "known to those skilled in the art", "prior art" or the like, the term derived is intended to cover those conventionally used in the field of the present application, but also cover those that are not currently known, whilst will become known in the art to be useful for the similar purposes.

In the context of this specification, the term "substantially", "about" or the like is intended to indicate that a deviation, such as within ±10%, within ±5%, within ±1%, within ±0.5% or within ±0.1%, is accepted as permissible or reasonable for any person skilled in the art.

In the context of the present specification, the term "reaction zone" is used in relation to a fluidized bed reactor. Desirably, a fluidized bed reactor includes a reaction zone, an inlet zone, and a separation zone. The "inlet zone" is the zone in the reactor through which the feedstock and catalyst are fed. The "reaction zone" is a zone in a reactor where the feed is contacted with a catalyst under conditions effective to convert the oxygenate of the feed to lower olefin products. The "separation zone" is a zone in the reactor where the catalyst and any other solids within the reactor are separated from the product. Typically, the reaction zone is located between the inlet zone and the separation zone.

In the context of this specification, the "gas phase" includes one or more of the raw methanol that is vaporized by heating, dilution gas (such as steam), and reaction products in gas phase (such as lower olefins, C4 hydrocarbons, etc.).

In the context of this specification, it is to be noted that the remainder volume of the reaction zone, excluding the volume occupied by the gas phase, is the volume of catalyst. The ratio of the volume of the gas phase to the volume of the catalyst indicates the volume fraction of the solid particles of the catalyst in the gas-solid two-phase mixture in the reaction zone.

In the context of this specification, the coke deposition amount (or average coke deposition amount) of the catalyst is calculated by the weight of coke deposit on the catalyst divided by the weight of the catalyst. The method for measuring the weight of the coke deposit on the catalyst comprises the following steps: weighing 0.1-1 g of the carbon-carrying catalyst, placing the catalyst in a high-temperature carbon analyzer for to combustion, and measuring the weight of carbon dioxide generated by combustion through infrared rays, to provide the weight of coke deposited on the catalyst. In order to determine the coke deposition amount of the catalyst in the reaction zone, aliquots of the catalyst in small equal amounts may be withdrawn continuously or periodically from various locations in the reaction zone.

In the context of this specification, catalyst deactivation in the fluidized bed reaction zone results in spent catalyst (catalyst to be regenerated), which is fed into a regenerator for regeneration to form regenerated catalyst (catalyst having been regenerated), which is returned to the fluidized bed reaction zone.

All percentages, parts, ratios, etc. involved in this specification are indicated by weight and pressures are gauge pressures unless explicitly indicated otherwise.

In the context of this specification, any two or more embodiments of the invention may be combined to form an embodiment, and the resulting embodiment is a part of the original disclosure of this specification, and is within the protection scope of the invention.

According to one embodiment of the invention, the invention relates to a process for producing lower olefins by using oxygenate. The process comprises the step of contacting an oxygenate feedstock in a fluidized bed reaction zone with a molecular sieve catalyst under effective conditions to produce a product comprising ethylene and propylene.

According to one embodiment of the invention, the oxygenate feedstock comprises an aliphatic alcohol comprising from 1 to 20 carbon atoms, preferably from 1 to 10 carbon atoms, more preferably from 1 to 4 carbon atoms. For example, methanol, ethanol, n-propanol, isopropanol, methyl ethyl ether, dimethyl ether, diethyl ether, diisopropyl ether, formaldehyde, dimethyl carbonate, dimethyl ketone, acetic acid, and mixtures thereof; preferably methanol, ethanol, dimethyl ether, diethyl ether, and mixtures thereof; more preferably methanol and dimethyl ether; more preferably methanol, can be used.

According to an embodiment of the invention, the effective conditions comprise: in the fluidized bed reaction zone, the proportion of the weight of the catalyst having a coke deposition amount of less than 3 wt % is 1-20 wt %, preferably 1-15 wt %, 1.5-10 wt %, or 2-5 wt %, based on the total weight of the catalysts in the fluidized bed reaction zone. The proportion of the catalyst having a coke deposition amount of less than 3 wt % in the total catalyst in the fluidized bed reaction zone is controlled by adjusting the circulating amount of the regenerated catalyst and the coke deposition amount of the regenerated catalyst (namely the coke burning degree of the regenerator).

According to one embodiment of the invention, the catalyst having a coke deposition amount of less than 3 wt % is distributed homogeneously in the fluidized-bed reaction zone.

According to an embodiment of the invention, the effective conditions further comprise: in the fluidized bed reaction zone, a ratio of the volume of the gas phase to the volume of the total catalyst of 1 to 15, preferably 5 to 12.

According to an embodiment of the invention, the effective conditions further comprise: a reaction temperature of 400-550° C., and a reaction pressure of 0-1 MPa.

According to one embodiment of the invention, the molecular sieve is a silicoaluminophosphate molecular sieve, preferably SAPO-18, SAPO-34, SAPO-5, or a combination thereof, and more preferably SAPO-34. The methods for preparing SAPO molecular sieves or SAPO molecular sieve catalysts are well known in the art.

According to one embodiment of the invention, the fluidized bed reaction zone is in a dense phase bed, turbulent bed, or fast fluidized bed, preferably a fast fluidized bed.

According to one embodiment of the present invention, the difference of the coke deposition amounts between the spent catalyst and the regenerated catalyst is not more than 7 wt %, preferably not more than 6 wt %, more preferably not more than 5 wt %. The coke deposition amount of the spent catalyst can be directly controlled through reaction, and the coke deposition amount of the regenerated catalyst can be controlled through the regeneration degree in the regenerator.

According to one embodiment of the invention, the gas phase and the catalyst in the fluidized bed reaction zone are rapidly separated by a separation device subsequent to the reaction or after leaving the fluidized bed reaction zone. The separation device is preferably a cyclonic separator.

Figure 1:
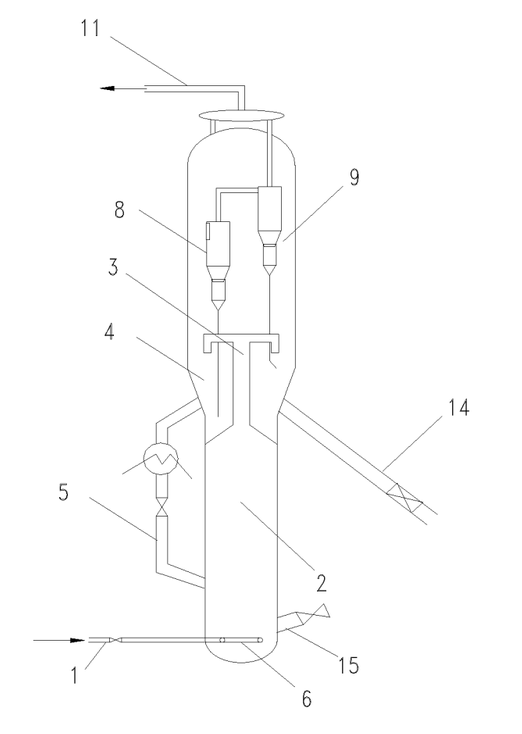
FIG. 1 is a schematic chart of a fluidized bed reactor according to the process of the present invention.

An exemplary embodiment 1 of the present invention is shown in FIG. 1. Referring to FIG. 1, the fluidized bed reactor used in the present invention is a fast fluidized bed, a dense phase fluidized bed or a turbulent fluidized bed, wherein a methanol feedstock is fed into the reactor through a feed line 1, and fed into the reaction zone 2 through a feedstock distributor 6, and contacted with a molecular sieve catalyst for reaction, to generate a product containing lower olefins, which at least partially deactivates the catalyst to form a spent catalyst. The spent catalyst is fed into the reactor separation zone 9 through a gas-solid rapid separation zone 3, wherein most of the catalyst separated by the gas-solid rapid separation device 3 is fed into the stripping zone 4, and the gas phase product and a part of the spent catalyst not separated by the gas-solid rapid separation device are fed into the cyclone separator 8 for separation again. The spent catalyst separated by the cyclone separator 8 is returned to the stripping zone 4 via the dipleg of the cyclone separator 8, while the separated gas product is passed to the subsequent separation section via an outlet line 11. The spent catalysts separated respectively by the gas-solid rapid separation zone 3 and by the cyclone separator 8 are combined, and are subsequently divided into two parts after being stripped by the stripping zone 4, where one part is returned to the bottom of the reaction zone 2 through a catalyst external circulation inclined line 5; while the other part is fed into the regenerator through a spent inclined line 14 for regeneration by coke burning, and the regenerated catalyst is returned to the reaction zone 2 through a regeneration inclined line 15.

EXAMPLES

The present invention will be described in further detail below by way of Examples and Comparative Examples, but the present invention is not limited to the following Examples.

Example I-1

A fast fluidized bed was used. A methanol feedstock (with a methanol purity of 95 wt %) was fed into the reaction zone of the fast fluidized bed, contacted an SAPO-34 molecular sieve catalyst, generating a product containing ethylene and propylene under effective conditions. The catalyst in the fluidized bed reaction zone was inactivated to form a spent catalyst, which spent catalyst was fed into a regenerator to be regenerated to form a regenerated catalyst, which regenerated catalyst was returned to the reaction zone of the fast fluidized bed. The difference between the coke deposition amounts of the spent catalyst and of the regenerated catalyst was 5 wt %. The gas phase and the catalyst in the fluidized bed reaction zone was rapidly separated through the separation device subsequent to the reaction or after leaving the fluidized bed reaction zone. The effective conditions comprised: a reaction temperature of 450° C., a reaction gauge pressure of 0.15 MPa, and calculated as the weight of the molecular sieve on the catalyst, in the reaction zone, the catalyst having a coke deposition amount of less than 3 wt % represented 14 wt %, the catalyst having a coke deposition amount of from 3 wt % to less than 5 wt % represented 68 wt %, and the catalyst having a coke deposition amount from 5 wt % to 10 wt % represented 16 wt %, and the ratio of the gas phase volume to the catalyst volume was 10. The sampling analysis results showed that the conversion of methanol was 99.96% and the selectivity to ethylene+ propylene on carbon basis was 84.52%.

Example I-2

A dense fluidized bed was used. A methanol feedstock (with a methanol purity of 95 wt %) was fed into the dense fluidized bed reaction zone, contacted an SAPO-34 molecular sieve catalyst, generating a product containing ethylene and propylene under effective conditions. The catalyst in the fluidized bed reaction zone was inactivated to form a spent catalyst, which spent catalyst was fed into a regenerator to be regenerated to form a regenerated catalyst, which regenerated catalyst was returned to the reaction zone of the fast fluidized bed. The difference between the coke deposition amounts of the spent catalyst and the regenerated catalyst was 6 wt %. The gas phase and the catalyst in the fluidized bed reaction zone was rapidly separated through the separation device subsequent to the reaction or after leaving the fluidized bed reaction zone. The effective conditions comprised: a reaction temperature of 550° C., a reaction gauge pressure of 1 MPa, and calculated as the weight of the molecular sieve on the catalyst, in the reaction zone, the catalyst having a coke deposition amount of less than 3 wt % represented 18 wt %, the catalyst having a coke deposition amount of from 3 wt % to less than 5 wt % represented 63 wt %, and the catalyst having a coke deposition amount from 5 wt % to 10 wt % represented 17 wt %, and the ratio of the gas phase volume to the catalyst volume was 1. The sampling analysis results showed that the conversion of methanol was 99.32% and the selectivity to ethylene+ propylene on carbon basis was 82.14%.

Example I-3

A turbulent fluidized bed was used. A methanol feedstock (with a methanol purity of 95 wt %) was fed into the turbulent fluidized bed reaction zone, contacted an SAPO-34 molecular sieve catalyst, generating a product containing ethylene and propylene under effective conditions. The catalyst in the fluidized bed reaction zone was inactivated to form a spent catalyst, which spent catalyst was fed into a regenerator to be regenerated to form a regenerated catalyst, which regenerated catalyst was returned to the reaction zone of the fast fluidized bed. The difference between the coke deposition amounts of the spent catalyst and the regenerated catalyst was 3 wt %. The gas phase and the catalyst in the fluidized bed reaction zone was rapidly separated through the separation device subsequent to the reaction or after leaving the fluidized bed reaction zone. The effective conditions comprised: a reaction temperature of 400° C., a reaction gauge pressure of 0.05 MPa, and calculated as the weight of the molecular sieve on the catalyst, in the reaction zone, the catalyst having a coke deposition amount of less than 3 wt % represented 15 wt %, the catalyst having a coke deposition amount of from 3 wt % to less than 5 wt % represented 66 wt %, and the catalyst having a coke deposition amount to from 5 wt % to 10 wt % represented 16 wt %, and the ratio of the gas phase volume to the catalyst volume was 3. The sampling analysis results showed that the conversion of methanol was 99.09% and the selectivity to ethylene+propylene on carbon basis was 83.99%.

Example I-4

A fast fluidized bed was used. A methanol feedstock (with the methanol purity of 99%) was fed into the reaction zone of the fast fluidized bed, contacted an SAPO-34 molecular sieve catalyst, generating a product containing ethylene and propylene under effective conditions. The catalyst in the fluidized bed reaction zone was inactivated to form a spent catalyst, which spent catalyst was fed into a regenerator to be regenerated to form a regenerated catalyst, which regenerated catalyst was returned to the reaction zone of the fast fluidized bed. The difference between the coke deposition amounts of the spent catalyst and the regenerated catalyst was 5 wt %. The gas phase and the catalyst in the fluidized bed reaction zone was rapidly separated through the separation device subsequent to the reaction or after leaving the fluidized bed reaction zone. The effective conditions comprised: a reaction temperature of 480° C., a reaction gauge pressure of 0.2 MPa, and calculated as the weight of the molecular sieve on the catalyst, in the reaction zone, the catalyst having a coke deposition amount of less than 3 wt % represented 5 wt %, the catalyst having a coke deposition amount of from 3 wt % to less than 5 wt % represented 50 wt %, and the catalyst having a coke deposition amount from 5 wt % to 10 wt % represented 42 wt %, and the ratio of the gas phase volume to the catalyst volume was 6. The sampling analysis results showed that the conversion of methanol was 99.90% and the selectivity to ethylene+propylene on carbon basis was 84.22%.

Example I-5

A methanol feedstock (with the methanol purity of 99%) was fed into the reaction zone of the fast fluidized bed, contacted an SAPO-34 molecular sieve catalyst, generating a product containing ethylene and propylene under effective conditions. The catalyst in the fluidized bed reaction zone was inactivated to form a spent catalyst, which spent catalyst was fed into a regenerator to be regenerated to form a regenerated catalyst, which regenerated catalyst was returned to the reaction zone of the fast fluidized bed. The difference between the coke deposition amounts of the spent catalyst and the regenerated catalyst was 6 wt %. The gas phase and the catalyst in the fluidized bed reaction zone was rapidly separated through the separation device subsequent to the reaction or after leaving the fluidized bed reaction zone. The effective conditions comprised: a reaction temperature of 480° C., a reaction gauge pressure of 0.15 MPa, and calculated as the weight of the molecular sieve on the catalyst, in the reaction zone, the catalyst having a coke deposition amount of less than 3 wt % represented 10 wt %, the catalyst having a coke deposition amount of from 3 wt % to less than 5 wt % represented 45 wt %, and the catalyst having a coke deposition amount from 5 wt % to 10 wt % represented 40 wt %, and the ratio of the gas phase volume to the catalyst volume was 12. The sampling analysis results showed that the conversion of methanol was 99.96% and the selectivity to ethylene+propylene on carbon basis was 84.78%.

Comparative Example I-1

The conditions and procedures described in Examples I-5 were followed except the catalyst having a coke deposition amount of less than 3 wt % represented 30 wt %, and the ratio of the gas phase volume to the catalyst volume was 0.5. The sampling analysis results showed that the conversion of methanol was 99.99% and the selectivity to ethylene+propylene on carbon basis was 80.32%.

Comparative Example I-2

The conditions and procedures described in Examples I-5 were followed except the catalyst having a coke deposition amount of less than 3 wt % represented 30 wt %, and the ratio of the gas phase volume to the catalyst volume was 20. The sampling analysis results showed that the conversion of methanol was 99.67% and the selectivity to ethylene+propylene on carbon basis was 79.61%.

Comparative Example I-3

The conditions and procedures described in Examples I-5 were followed except the catalyst having a coke deposition amount of less than 3 wt % represented 10 wt %, and the ratio of the gas phase volume to the catalyst volume was 20. The sampling analysis results showed that the conversion of methanol was 99.07% and the selectivity to ethylene+propylene on carbon basis was 83.98%.

Comparative Example I-4

The conditions and procedures described in Examples I-5 were followed except the catalyst having a coke deposition amount of less than 3 wt % represented 0.5 wt %, and the ratio of the gas phase volume to the catalyst volume was 12. The sampling analysis results showed that the conversion of methanol was 99.01% and the selectivity to ethylene+propylene on carbon basis was 83.76%.

Comparative Example I-5

The conditions and procedures described in Examples I-5 were followed except that the difference between the coke deposition amounts of the spent catalyst and the regenerated catalyst was 9 wt % The sampling analysis results showed that the conversion of methanol was 98.97% and the selectivity to ethylene+propylene on carbon basis was 83.55%.

Obviously, the process according to the present invention could achieve the purpose of improving the yield of the lower olefins and thus was able to be used for the industrial production of the lower olefins.

Example II-1

A fast fluidized bed was used. A methanol feedstock (with a methanol purity of 95 wt %) was fed into the reaction zone of the fast fluidized bed, contacted an SAPO-34 molecular sieve catalyst, generating a product containing ethylene and propylene under effective conditions. The catalyst in the fluidized bed reaction zone was inactivated to form a spent catalyst, which spent catalyst was fed into a regenerator to be regenerated to form a regenerated catalyst, which regenerated catalyst was returned to the reaction zone of the fast fluidized bed. The outlet of the regeneration line was equipped with a catalyst distributor, which catalyst distributor was horizontally arranged along the radial direction of the fluidized bed reactor, to uniformly distribute the regenerated catalyst on the radial plane of the fluidized bed reactor reaction zone. The catalyst distributor was supplied with delivering medium of steam. The fluidized bed in the reaction zone of the fluidized bed reactor was divided into a dense phase zone and a dilute phase zone, where the range in height positioned from the distributor up to a height at ½ bed height distancing from the distributor composed the dense phase zone of the fluidized bed (for the fast fluidized bed type, the height of the dense phase zone was the height of the reaction zone); and the coke deposition amounts on the catalyst particles within the height range from the distributor up to a height at ½ bed height distancing from the distributor varied to have a maximum difference of 3.3%. The effective reaction conditions comprised: a reaction temperature of 480° C., and a reaction gauge pressure of 0.15 MPa. The ratio of the regenerated catalyst to the spent catalyst in the reaction zone was controlled to be 0.1, and the coke deposition amount on the regenerated catalyst was 1.0 wt %. The methanol conversion in the zone from the distributor up to a height at ½ bed height distancing from the distributor was 85%. The sampling analysis results showed that at the reactor outlet, the conversion of methanol was 99.95% and the selectivity to ethylene+propylene on carbon basis was 84.36%.

Example II-2

The conditions and procedures described in Example II-1 were followed. A methanol feedstock (with a methanol purity of 95 wt %) was fed into the reaction zone of the fast fluidized bed, contacted an SAPO-34 molecular sieve catalyst, generating a product containing ethylene and propylene under effective conditions. The catalyst in the fluidized bed reaction zone was inactivated to form a spent catalyst, which spent catalyst was fed into a regenerator to be regenerated to form a regenerated catalyst, which regenerated catalyst was returned to the reaction zone of the fast fluidized bed. The outlet of the regeneration line was equipped with a catalyst distributor, which catalyst distributor was horizontally arranged along the radial direction of the fluidized bed reactor, to uniformly distribute the regenerated catalyst on the radial plane of the fluidized bed reactor reaction zone. The catalyst distributor was supplied with delivering medium of steam. The fluidized bed in the reaction zone of the fluidized bed reactor was divided into a dense phase zone and a dilute phase zone, where the range in height positioned from the distributor up to a height at ½ bed height distancing from the distributor composed the dense phase zone of the fluidized bed; and the coke deposition amounts on the catalyst particles within the height range from the distributor up to a height at ½ bed height distancing from the distributor varied to have a maximum difference of 2.5%. The effective reaction conditions comprised: a reaction temperature of 480° C., and a reaction gauge pressure of 0.01 MPa. The ratio of the regenerated catalyst to the spent catalyst in the reaction zone was controlled to be 0.3; and the coke deposition amount on the regenerated catalyst was 2 wt %. The methanol conversion in the zone from the distributor up to a height at ½ bed height distancing from the distributor was 82%. The sampling analysis results showed that at the reactor outlet, the conversion of methanol was 99.61% and the selectivity to ethylene+propylene on carbon basis was 86.55%.

Example II-3

The conditions and procedures described in Example II-1 were followed. A methanol feedstock (with a methanol purity of 95 wt %) was fed into the reaction zone of the fast fluidized bed, contacted an SAPO-34 molecular sieve catalyst, generating a product containing ethylene and propylene under effective conditions. The catalyst in the fluidized bed reaction zone was inactivated to form a spent catalyst, which spent catalyst was fed into a regenerator to be regenerated to form a regenerated catalyst, which regenerated catalyst was returned to the reaction zone of the fast fluidized bed. The outlet of the regeneration line was equipped with a catalyst distributor, which catalyst distributor was horizontally arranged along the radial direction of the fluidized bed reactor, to uniformly distribute the regenerated catalyst on the radial plane of the fluidized bed reactor reaction zone. The catalyst distributor was supplied with delivering medium of steam. The fluidized bed in the reaction zone of the fluidized bed reactor was divided into a dense phase zone and a dilute phase zone, where the range in height positioned from the distributor up to a height at ½ bed height distancing from the distributor composed the dense phase zone of the fluidized bed; and the coke deposition amounts on the catalyst particles within the height range from the distributor up to a height at ½ bed height distancing from the distributor varied to have a maximum difference of 7%. The effective reaction conditions comprised: a reaction temperature of 550° C., and a reaction gauge pressure of 1.0 MPa. The ratio of the regenerated catalyst to the spent catalyst in the reaction zone was controlled to be 0.05; and the coke deposition amount on the regenerated catalyst was 0.01 wt %. The methanol conversion in the zone from the distributor up to a height at ½ bed height distancing from the distributor was 91%. The sampling analysis results showed that at the reactor outlet, the conversion of methanol was 99.99% and the selectivity to ethylene+propylene on carbon basis was 83.59%.

Example II-4

The conditions and procedures described in Example II-1 were followed. A methanol feedstock (with a methanol purity of 95 wt %) was fed into the reaction zone of the fast fluidized bed, contacted an SAPO-34 molecular sieve catalyst, generating a product containing ethylene and propylene under effective conditions. The catalyst in the fluidized bed reaction zone was inactivated to form a spent catalyst, which spent catalyst was fed into a regenerator to be regenerated to form a regenerated catalyst, which regenerated catalyst was returned to the reaction zone of the fast fluidized bed. The outlet of the regeneration line was equipped with a catalyst distributor, which catalyst distributor was horizontally arranged along the radial direction of the fluidized bed reactor, to uniformly distribute the regenerated catalyst on the radial plane of the fluidized bed reactor reaction zone. The catalyst distributor was supplied with delivering medium of steam. The fluidized bed in the reaction zone of the fluidized bed reactor was divided into a dense phase zone and a dilute phase zone, where the range in height positioned from the distributor up to a height at ½ bed height distancing from the distributor composed the dense phase zone of the fluidized bed; and the coke deposition amounts on the catalyst particles within the height range from the distributor up to a height at ½ bed height distancing from the distributor varied to have a maximum difference of 4.5%. The effective reaction conditions comprised: a reaction temperature of 490° C., and a reaction gauge pressure of 0.17 MPa. The ratio of the regenerated catalyst to the spent catalyst in the reaction zone was controlled to be 0.08; and the coke deposition amount on the regenerated catalyst was 0.5 wt %. The methanol conversion in the zone from the distributor up to a height at ½ bed height distancing from the distributor was 88%. The sampling analysis results showed that at the reactor outlet, the conversion of methanol was 99.98% and the selectivity to ethylene+propylene on carbon basis was 85.19%.

Example II-5

The conditions and procedures described in Example II-1 were followed. A methanol feedstock (with a methanol purity of 95 wt %) was fed into the reaction zone of the fast fluidized bed, contacted an SAPO-34 molecular sieve catalyst, generating a product containing ethylene and propylene under effective conditions. The catalyst in the fluidized bed reaction zone was inactivated to form a spent catalyst, which spent catalyst was fed into a regenerator to be regenerated to form a regenerated catalyst, which regenerated catalyst was returned to the reaction zone of the fast fluidized bed. The outlet of the regeneration line was equipped with a catalyst distributor, which catalyst distributor was horizontally arranged along the radial direction of the fluidized bed reactor, to uniformly distribute the regenerated catalyst on the radial plane of the fluidized bed reactor reaction zone. The catalyst distributor was supplied with delivering medium of steam. The fluidized bed in the reaction zone of the fluidized bed reactor was divided into a dense phase zone and a dilute phase zone, where the range in height positioned from the distributor up to a height at ½ bed height distancing from the distributor composed the dense phase zone of the fluidized bed; and the coke deposition amounts on the catalyst particles within the height range from the distributor up to a height at ½ bed height distancing from the distributor varied to have a maximum difference of 1.5%. The effective reaction conditions comprised: a reaction temperature of 490° C., and a reaction gauge pressure of 0.15 MPa. The ratio of the regenerated catalyst to the spent catalyst in the reaction zone was controlled to be 0.5; and the coke deposition amount on the regenerated catalyst was 5 wt %. The methanol conversion in the zone from the distributor up to a height at ½ bed height distancing from the distributor was 86%. The sampling analysis results showed that at the reactor outlet, the conversion of methanol was 99.92% and the selectivity to ethylene+propylene on carbon basis was 85.99%.

Example II-6

The conditions and procedures described in Example II-1 were followed. A methanol feedstock (with a methanol purity of 95 wt %) was fed into the reaction zone of the fast fluidized bed, contacted an SAPO-34 molecular sieve catalyst, generating a product containing ethylene and propylene under effective conditions. The catalyst in the fluidized bed reaction zone was inactivated to form a spent catalyst, which spent catalyst was fed into a regenerator to be regenerated to form a regenerated catalyst, which regenerated catalyst was returned to the reaction zone of the fast fluidized bed. The outlet of the regeneration line was equipped with a catalyst distributor, which catalyst distributor was horizontally arranged along the radial direction of the fluidized bed reactor, to uniformly distribute the regenerated catalyst on the radial plane of the fluidized bed reactor reaction zone. The catalyst distributor was supplied with delivering medium of steam. The fluidized bed in the reaction zone of the fluidized bed reactor was divided into a dense phase zone and a dilute phase zone, where the range in height positioned from the distributor up to a height at ½ bed height distancing from the distributor composed the dense phase to zone of the fluidized bed; and the coke deposition amounts on the catalyst particles within the height range from the distributor up to a height at ½ bed height distancing from the distributor varied to have a maximum difference of 3%. The effective reaction conditions comprised: a reaction temperature of 400° C., and a reaction gauge pressure of 0.01 MPa. The ratio is of the regenerated catalyst to the spent catalyst in the reaction zone was controlled to be 0.05; and the coke deposition amount on the regenerated catalyst was 0.5 wt %. The methanol conversion in the zone from the distributor up to a height at ½ bed height distancing from the distributor was 81%. The sampling analysis results showed that at the reactor outlet, the conversion of methanol was 99.51% and the selectivity to ethylene+propylene on carbon basis was 84.80%.

Example II-7

The conditions and procedures described in Example II-1 were followed. A methanol feedstock (with a methanol purity of 95 wt %) was fed into the reaction zone of the fast fluidized bed, contacted an SAPO-34 molecular sieve catalyst, generating a product containing ethylene and propylene under effective conditions. The catalyst in the fluidized bed reaction zone was inactivated to form a spent catalyst, which spent catalyst was fed into a regenerator to be regenerated to form a regenerated catalyst, which regenerated catalyst was returned to the reaction zone of the fast fluidized bed. The outlet of the regeneration line was equipped with a catalyst distributor, which catalyst distributor was horizontally arranged along the radial direction of the fluidized bed reactor, to uniformly distribute the regenerated catalyst on the radial plane of the fluidized bed reactor reaction zone. The catalyst distributor was supplied with delivering medium of steam. The fluidized bed in the reaction zone of the fluidized bed reactor was divided into a dense phase zone and a dilute phase zone, where the range in height positioned from the distributor up to a height at ½ bed height distancing from the distributor composed the dense phase zone of the fluidized bed; and the coke deposition amounts on the catalyst particles within the height range from the distributor up to a height at ½ bed height distancing from the distributor varied to have a maximum difference of 8%. The effective reaction conditions comprised: a reaction temperature of 550° C., and a reaction gauge pressure of 0.75 MPa. The ratio of the regenerated catalyst to the spent catalyst in the reaction zone was controlled to be 0.15; and the coke deposition amount on the regenerated catalyst was 0.1 wt %. The methanol conversion in the zone from the distributor up to a height at ½ bed height distancing from the distributor was 93%. The sampling analysis results showed that at the reactor outlet, the conversion of methanol was 99.99% and the selectivity to ethylene+propylene on carbon basis was 84.33%.

Comparative Example II-1

The conditions and procedures described in Example I-5 were followed except that the coke deposition amounts on the catalyst particles within the height range from the distributor up to a height at ½ bed height distancing from the distributor varied to had a maximum difference of 10%. The methanol conversion in the zone from the distributor up to a height at ½ bed height distancing from the distributor was 71%. The sampling analysis results showed that at the reactor outlet, the conversion of methanol was 99.01% and the selectivity to ethylene+propylene on carbon basis was 81.78%.

Obviously, the process according to the present invention could achieve the purpose of improving the yield of the lower olefins and thus was able to be used for the industrial production of the lower olefins.

The invention claimed is:

1. A process for producing lower olefins from oxygenates, comprising the steps of contacting a feedstock comprising oxygenates with molecular sieve catalyst in fluidized bed reaction zone under effective conditions, to produce product comprising ethylene and/or propylene;
    wherein the effective conditions comprise that in the fluidized bed reaction zone, the weights of catalysts having various carbon deposition amounts are controlled, calculated as the weight of the molecular sieve in the catalysts, to have the following proportions based on the total weight of the catalysts in the fluidized bed reaction zone:
    the proportion of the weight of the catalyst having a coke deposition amount of less than 3 wt % is 1-20 wt %, based on the total weight of the catalysts in the fluidized bed reaction zone;
    the catalyst having a coke deposition amount of from 3 wt % to less than 5 wt % represents 10 to 70 wt %, based on the total weight of the catalysts; and
    the catalyst having a coke deposition amount from 5 wt % to 10 wt % represents 10 to 88 wt %, based on the total weight of the catalysts.

2. The process according to claim 1, wherein the ratio of the volume of the gas phase in the fluidized bed reaction zone to the volume of the total catalyst in the fluidized bed reaction zone is from 1 to 15.

3. The process according to claim 1, wherein the feedstock is fed through a distribution device into the reaction zone of the fluidized bed reactor, wherein the coke deposition amounts on the catalyst particles within the height range from the distribution device up to a height at ½ bed height vary to have a maximum difference of less than 8 wt %.

4. The process according to claim 3, wherein the coke deposition amounts on the catalyst particles within the height range from the distribution device up to a height at ½ bed height vary to have a maximum difference of greater than 0.1 wt %.

5. The process of claim 3, wherein the spent catalyst is derived from deactivation of the catalyst in the reaction zone, the spent catalyst is introduced into a regenerator through a spent inclined line to be regenerated to form a regenerated catalyst, and the regenerated catalyst is returned to the reaction zone of the fast fluidized bed through a regeneration inclined line; wherein the ratio of the regenerated catalyst to the spent catalyst in the reaction zone is controlled to be 0.01-1; and the coke deposition amount on the regenerated catalyst is 0 to 5 wt %.

6. The process according to claim 1, wherein the oxygenate feedstock comprises methanol.

7. The process according to claim 1, wherein the molecular sieve is a silicoaluminophosphate molecular sieve.

8. The process according to claim 1, wherein the fluidized bed reaction zone is in the form of a dense phase bed, turbulent bed, or fast fluidized bed.

9. The process according to claim 1, wherein the effective conditions further comprise: a reaction temperature of 400-550° C., and a reaction pressure of 0-1 MPaG.

10. The process according to claim 1, wherein the difference of the coke deposition amounts between the spent catalyst and the regenerated catalyst is not more than 7 wt %.

11. The process according to claim 1, wherein the catalyst having a coke deposition amount of less than 3 wt % is uniformly distributed within the fluidized bed reaction zone.

12. The process according to claim 1, wherein the gas phase and the catalyst within the fluidized bed reaction zone are rapidly separated by a separation device subsequent to the reaction or after leaving the fluidized bed reaction zone.

13. A fluidized bed reactor for carrying out the process according to claim 1 for producing lower olefins from oxygenates, comprising:
    a reaction zone, for receiving a methanol feedstock and contacting it with a catalyst to produce an olefin product, wherein the process deactivates, at least in part, the catalyst to produce a spent catalyst;
    a gas-solid rapid separation device, for separating the spent catalyst from the reaction zone;
    a cyclone separator, for receiving the gas-phase product separated by the gas-solid rapid separation device and a part of the spent catalyst not separated by the gas-solid rapid separation device, so as to carry out a secondary separation;
    a stripping zone, for receiving the spent catalyst from the dipleg of the cyclone; and
    an external circulation inclined line for catalyst, for returning at least a part of stripped spent catalyst from the stripping zone to the bottom of the reaction zone.

14. The fluidized bed reactor according to claim 13, further comprising a separation zone between the reaction zone and the gas-solid rapid separation device, for allowing at least a part of the spent catalyst to settle for a preliminary separation from the gas phase.

15. A process for producing lower olefins from oxygenates, comprising the steps of: contacting the oxygenate feedstock with a molecular sieve catalyst in a fluidized bed reaction zone under effective conditions, to produce an ethylene and/or propylene containing product;
    wherein the feedstock is fed into the fluidized bed reactor reaction zone through a distributor, wherein the coke deposition amounts on the catalyst particles within the height range from the distributor up to a height at ½ bed height distancing from the distributor vary to have a maximum difference of less than 8 wt %.

16. The process according to claim 15, wherein the coke deposition amounts on the catalyst particles within the height range from the distributor up to a height at ½ bed height distancing from the distributor vary to have a maximum difference of greater than 0.1 wt %.

17. The process according to claim 15, wherein a spent catalyst is derived from deactivation of the catalyst in the reaction zone, the spent catalyst is introduced into a regenerator through a spent inclined line to be regenerated to form a regenerated catalyst, and the regenerated catalyst is returned to the reaction zone of the fast fluidized bed through a regeneration inclined line.

18. The process according to claim 17, wherein a difference of the coke deposition amounts between the spent catalyst and the regenerated catalyst is not more than 7 wt %.

* * * * *